United States Patent [19]

Berger

[11] 4,370,130

[45] Jan. 25, 1983

[54] WAX OCCLUSAL RIM WARMER

[76] Inventor: Igor A. Berger, 25875 Greenfield, Southfield, Mich. 48075

[21] Appl. No.: 279,407

[22] Filed: Jul. 1, 1981

[51] Int. Cl.³ .............................................. A61C 13/20
[52] U.S. Cl. ....................................... 433/32; 219/241
[58] Field of Search .................. 433/32; 219/421, 219, 219/220, 242

[56] References Cited

U.S. PATENT DOCUMENTS

| 2,636,970 | 4/1953 | Jackson et al. | 433/32 |
| 3,769,495 | 10/1973 | Orfei | 219/220 |
| 3,902,043 | 8/1975 | Rogzn | 433/32 |

Primary Examiner—Robert Peshock
Attorney, Agent, or Firm—Krass, Young & Schivley

[57] ABSTRACT

An apparatus for melting the occlusal surface of wax occlusal rims to approximate the patient's proper plane of occlusion. The apparatus includes a heated planar member inclined from horizontal to produce gravity induced flow of melted wax into a receptacle.

1 Claim, 3 Drawing Figures

WAX OCCLUSAL RIM WARMER

BACKGROUND OF THE INVENTION

1. Field of the Invention

This invention relates to an apparatus for shaping wax occlusal rims. The apparatus includes a heated flat surface for melting the occlusal surface of a wax occlusal rim to establish the proper bite orientation.

2. Prior Art

Wax occlusal rims are used to obtain an impression of a patient's maxilla and mandibula and to establish the vertical dimension of occlusion as an intermediate step in the fabrication of artificial dentures. Each individual patient's occlusal vertical dimension (OVD) must be determined by the prosthodontist to assure proper denture fit. The patient's mouth is first measured to determine the tentative occlusal plane. The maxillary and mandibulary wax occlusal rims are then inserted in the patient's mouth and compared to the tentative occlusal plane measurements and checked by various physiological methods for proper fit. Any variance from the proper fit is eliminated by adding wax to the occlusal surface if the OVD is insufficient or by melting wax from the occlusal surface if the OVD is excessive.

A prosthodontist usually forms wax occlusal rims with a putty knife. To reduce the OVD the putty knife is first heated over an open flame and is then pressed against the base of the wax bite rim to melt it to the required dimension. The putty knife is held in one hand while the wax bite rim is retained by the other hand. To increase the OVD an additional segment of wax is warmed by pressing against the heated putty knife and then applied to the occlusal surface. The procedure is repeated until the proper fit is obtained. The putty knife is awkward to use and the angle of wax removal is difficult to control. The temperature of the putty knife is also difficult to control resulting in variation in the rate of wax removal and additional inaccuracy.

The wax removed from the occlusal rim is normally permitted to drip uncontrolled from the putty knife to the floor or work table, requiring subsequent cleaning.

It is an object of this invention to provide an apparatus for accurately removing wax from an occlusal rim featuring a stationary work surface which allows the prosthodontist to easily and quickly shape the wax occlusal rim.

Another object of this invention is to provide a device for shaping wax occlusal rims having a work surface disposed at an angle inclined from horizontal and having temperature control means.

Another object of the invention is to provide a safe, effective apparatus for melting a portion of an occlusal rim while minimizing the chance of injury from handling hot tools or from working over an open flame.

Another object of the invention is to provide a tool for removing wax from occlusal rims that retains the removed wax in a container, thus keeping floor and work surfaces clean while permitting reuse of the removed wax.

SUMMARY OF THE INVENTION

According to the present invention, a simple, effective apparatus for forming an occlusal rim is provided comprising a stationary inclined planar member, a heating element adjacent to the planar member for heating the planar member so that a occlusal rim may be shaped by either melting the wax of the occlusal surface by pressing against the planar member or by heating wax segments to be added to the occlusal surface. The planar member features a raised periphery and a drainage slot for guiding the flow of melted wax into a wax receptacle. The receptacle is removable and the wax retained within the receptacle is recycleable.

In a preferred embodiment the heat source is adjustable to allow for controlled wax removal.

DISCLOSURE OF THE INVENTION

Figure 1:
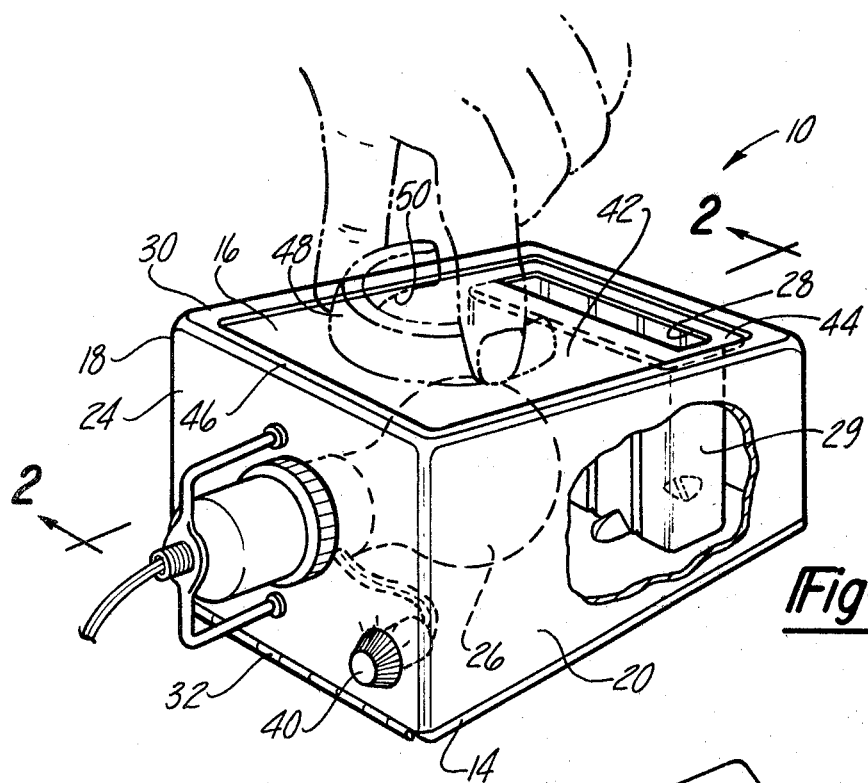
FIG. 1 is a perspective view of the apparatus according to the present invention.

Referring to FIG. 1, a warmer for wax occlusal rims is indicated generally by the reference numeral 10. The warmer 10 includes a body 12 preferably formed of metal, such as aluminum or steel, and a base 14. The body 12 includes a top 16, two side walls 18 and 20, a front wall 22, and a rear wall 24. The rear wall 24 is of greater vertical extent than the front wall 22 and the top 16 is disposed at an angle relative to the horizontal plane. A light bulb 26 is attached to the rear wall 24 to extend inside the body 12 adjacent to the top 16. A wax drainage slot 28 is provided in the top 16 to permit wax (not shown) to drain therethrough into a wax receptacle 29. The peripheral edge 30 of the top 16 is slightly raised to prevent any melted wax from spilling off of the top 16.

In one embodiment, the body 12 is made in one piece from a cast aluminum box having four sides and a bottom. The top edges of the sides are cut off at an angle so that the top 16 of the box member 12 is disposed at an angle when the box is inverted. Alternatively, the top 16 of the box member 12 may be formed of sheet metal and attached to the upper edge of said walls 18, 20, 22 and 24. The rear wall 24 of the body 12 is connected by a hinge 32 to the base 14. The base 14 may be constructed of fiberboard or another insulative material. The body 12 is adapted to be raised, as shown in phantom lines in FIG. 2, to permit access to the interior of the device.

Figure 3:
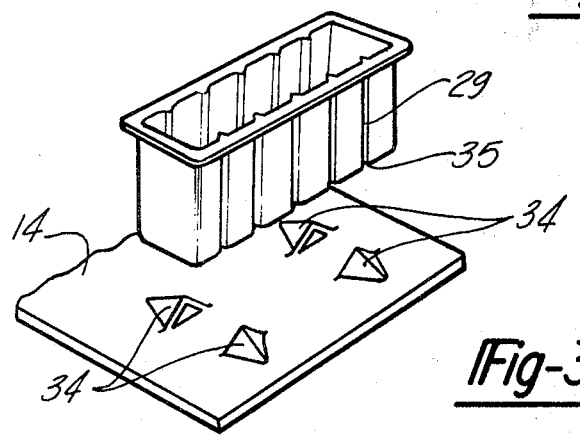
FIG. 3 is a cutaway view of the way receptacle and its retaining means.

As best shown in FIG. 3, the base 14 has a plurality of gripping members 34 formed integrally therewith or attached thereto for removably retaining the wax receptacle 29.

The wax receptacle 29 is mounted on the base 14 beneath the slot 28 to assure collection of all wax melted on the top 16. The wax receptacle 29 may be formed of aluminum sheet or foil to be disposable. One or more sides of the wax receptacle 29 may have indentations 35 formed therein to facilitate sectioning the collected wax after hardening for reuse.

Figure 2:
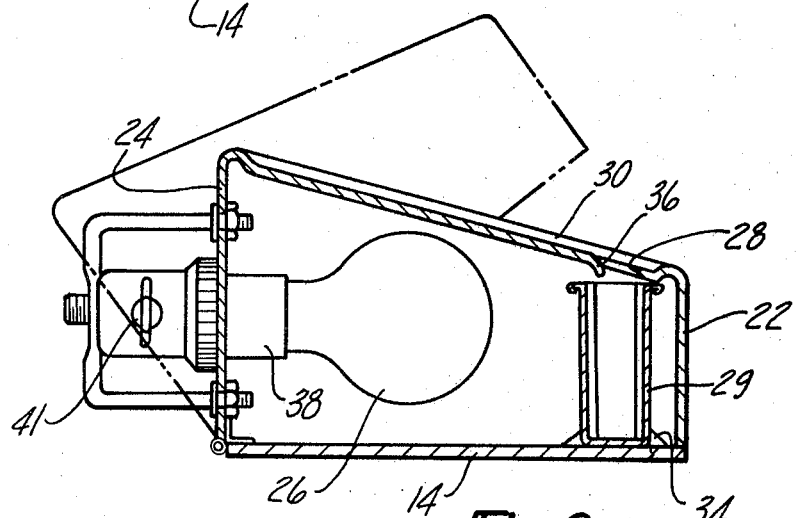
FIG. 2 is a section view of the apparatus taken along the line 2—2 in FIG. 1.

As shown in FIG. 2, the slot 28 has an upper edge 36 that is flanged downwardly to channel the flow of melted wax into the wax receptacle 29.

The heat source used to warm the top 16 in the preferred embodiment is a light bulb 26. The light bulb 26 is attached to a receptacle 38 that is attached to the rear wall 24. In a preferred embodiment the temperature of the top surface may be controlled by a rheostat 40, a light switch 41 or equivalent electrical control for regulating the current supplied to the light bulb 26. Alternatively, any equivalent heating element could be used to heat the device.

The top 16 of the heater 10 includes a substantially planar work surface 42 bordered by the raised peripheral edge 30 and has a slot 28 at a lower end 44. The top 16 is disposed at an angle wherein the lower end 44 is below the upper end 46 so that melted wax will flow from the work surface 42 to the slot 28. The wax receptacle 29 is positioned below the slot 28 to collect the melted wax flowing through the slot 28.

INDUSTRIAL APPLICABILITY

In operation, the wax occlusal rim warmer is placed on a table and the light bulb 26 is energized to warm the work surface 42. When the work surface 42 has been heated to a temperature above the melting point of the wax of the occlusal rim 48, it is ready for operation. The occlusal rim 48 is shaped by pressing the occlusal surface 50 of the occlusal rim against the work surface 42 until the occlusal surface 40 conforms to the patient's occlusal plane. If it is necessary to increase the occlusal vertical dimension, additional segments of wax may be warmed by pressing against the work surface and then attached to the occlusal surface 50.

When the occlusal rim 48 is pressed against the work surface 42, the melted wax flows down the work surface 42 and drops through the slot 28 into the wax receptacle 29 located inside the warmer 10. The wax receptacle 29 may be removed, emptied and replaced or disposed of when an accumulation of wax has been deposited in the receptacle 29. The indentations 35 in the wax receptacle 29 are designed to facilitate splitting the hardened wax into smaller sections for reuse.

It is to be understood that the invention has been described with reference to a specific embodiment with various modifications being possible and that the foregoing description is not to be construed in a limiting sense.

The embodiments of the invention in which an exclusive property or privilege is claimed are defined as follows:

1. Apparatus for removing material from a wax occlusal rim to establish the occlusal plane of the corresponding prosthodontic device comprising:
   a body having side walls, a base adapted to be disposed on a supporting surface, and a planar top formed of metal, the top being supported on the side walls at an acute angle relative to the base;
   a rectangular receptacle extending within the body and having an open upper end fixed to a slot formed in the top adjacent the edge thereof closest to the base;
   an electric light bulb supported within the body with its bulb in proximity to the side of the top facing the base; and
   means for energizing the light bulb to heat the planar top whereby a wax occlusal rim may be modified in form by pressing it into contact with the planar top, and wax melted from the rim will fall into said container.

* * * * *